US012667322B2

(12) United States Patent
Cimen et al.

(10) Patent No.: US 12,667,322 B2
(45) Date of Patent: Jun. 30, 2026

(54) SCORING AND RANKING ANGIOGRAMS

(71) Applicant: SIEMENS HEALTHINEERS AG,
Forchheim (DE)

(72) Inventors: Serkan Cimen, Jersey City, NJ (US);
Dominik Neumann, Erlangen (DE);
Tiziano Passerini, Plainsboro, NJ (US)

(73) Assignee: Siemens Healthineers AG, Forchheim
(DE)

( * ) Notice: Subject to any disclaimer, the term of this
patent is extended or adjusted under 35
U.S.C. 154(b) by 328 days.

(21) Appl. No.: 18/454,102

(22) Filed: Aug. 23, 2023

(65) Prior Publication Data

US 2024/0099683 A1 Mar. 28, 2024

(30) Foreign Application Priority Data

Sep. 26, 2022 (EP) .................................... 22197745

(51) Int. Cl.
*A61B 6/50* (2024.01)
*A61B 6/46* (2024.01)
(Continued)

(52) U.S. Cl.
CPC .............. *A61B 6/504* (2013.01); *A61B 6/463*
(2013.01); *G06T 7/0012* (2013.01); *G16H*
*50/20* (2018.01);
(Continued)

(58) Field of Classification Search
CPC ....... A61B 6/504; A61B 6/463; A61B 6/4441;
A61B 6/481; G06T 7/0012;
(Continued)

(56) References Cited

U.S. PATENT DOCUMENTS 7,840,076 B2 11/2010 Bouguet et al.
8,566,331 B1 10/2013 Covell et al.
(Continued)

FOREIGN PATENT DOCUMENTS

WO WO-2020172999 A1 * 9/2020 ........... G06T 7/0012

OTHER PUBLICATIONS

Li, Hang. "A short introduction to learning to rank." IEICE Transactions on Information and Systems 94.10 (2011): 1854-1862.
(Continued)

*Primary Examiner* — Siamak Harandi

(57) ABSTRACT

Techniques for processing one or more frames of an angiogram are disclosed. The processing may take place during or after an angiography exam. The one or more frames of the angiogram are acquired during the angiography exam. The one or more frames are processed to determine, based on at least one pre-defined criterion, whether the angiogram at least comprises one frame with a diagnostic value among the one or more frames. If the angiogram comprises at least one frame with the diagnostic value, based on the angiogram, a score quantifying the diagnostic value of the angiogram is determined using a trained machine-learning (ML) algorithm. Techniques for processing, e.g., ranking/sorting, multiple angiograms associated with an anatomical region of interest of a patient are also provided, by which a respective score for each of the multiple angiograms is determined using the techniques for processing one or more frames of an angiogram.

17 Claims, 4 Drawing Sheets

(51) Int. Cl.
     G06T 7/00        (2017.01)
     G16H 50/20      (2018.01)

(52) U.S. Cl.
     CPC .............. *G06T 2207/20081* (2013.01); *G06T 2207/30104* (2013.01)

(58) Field of Classification Search
     CPC . G06T 2207/20081; G06T 2207/30104; G06T 2207/10081; G06T 2207/10121; G06T 2207/20084; G06T 2207/30048; G16H 50/20
     See application file for complete search history.

(56) References Cited

U.S. PATENT DOCUMENTS

| | | | |
|---|---|---|---|
| 9,659,384 B2 | 5/2017 | Shaji et al. | |
| 10,140,421 B1 * | 11/2018 | Bernard | ............... G06V 10/764 |
| 11,227,384 B2 | 1/2022 | Kashyap et al. | |
| 2018/0042566 A1 * | 2/2018 | Roffé | ................... A61B 6/4441 |
| 2020/0258215 A1 * | 8/2020 | Kashyap | ................ G06V 10/82 |
| 2021/0374447 A1 * | 12/2021 | Liu | ............................ G06T 5/20 |
| 2022/0092776 A1 | 3/2022 | Ehlers et al. | |
| 2024/0273723 A1 * | 8/2024 | Tison | ................... A61B 8/0891 |

OTHER PUBLICATIONS

Lu, Bin, et al. "Comparison of diagnostic accuracy and radiation dose between prospective triggering and retrospective gated coronary angiography by dual-source computed tomography." The American journal of cardiology 107.9 (2011): 1278-1284.

Zhou, B., Khosla, A., Lapedriza, A., Oliva, A. and Torralba, A., 2016. Learning deep features for discriminative localization. In Proceedings of the IEEE conference on computer vision and pattern recognition (pp. 2921-2929).

Zhou, Chengyang, et al. "Automated deep learning analysis of angiography video sequences for coronary artery disease." arXiv preprint arXiv:2101.12505 (2021).

Extended European Search Report (EESR) mailed Mar. 16, 2023 in corresponding European Patent Application No. 22197745.7.

* cited by examiner

4000 obtaining multiple angiograms associated with an anatomical region of interest of a patient — 4100 determining, for each of the multiple angiograms, a score quantifying a diagnostic value of the angiogram — 4200 sorting the multiple angiograms by score descending — 4300

9000

Processor          Memory 9020          9010          9030

Interface

SCORING AND RANKING ANGIOGRAMS

RELATED APPLICATION

This application claims the benefit of EP 22197745.7, filed on Sep. 26, 2022, which is hereby incorporated by reference in its entirety.

TECHNICAL FIELD

Various examples of the disclosure generally relate to angiography. Various examples specifically relate to processing angiograms acquired during an angiography exam to quantify a diagnostic value of the respective angiograms.

BACKGROUND

Angiography (or arteriography) is a medical imaging technique used to visualize the inside, or lumen, of blood vessels and organs of the body, with a particular interest in the arteries, veins, and heart chambers. Modern angiography is performed by injecting a radio-opaque contrast agent into the blood vessel and imaging using X-ray based techniques such as fluoroscopy. The acquired film or video (i.e., a sequence of images) of the blood vessels is called an angiograph, or more commonly an angiogram. I.e., each angiogram includes multiple frames. Different ones of the multiple frames correspond to different distribution phases of the contrast agent throughout the body or organ.

In clinical practice, angiography may be used to image the heart and nearby blood vessels (called coronary angiography), to image the blood vessels in and around the brain (called cerebral angiography), to image the blood vessels supplying the lung (called pulmonary angiography), to image the blood vessels supplying the kidneys (called renal angiography), or to image the eyes (called fluorescein angiography).

An angiography study (or exam) includes acquisitions of several angiograms. For example, a coronary angiography exam includes acquisitions of several angiograms of both coronary arteries acquired from multiple angulations. The angiography exam can take between 30 minutes and 2 hours.

During an angiography exam, a radio-opaque contrast agent is injected into the blood vessels.

Exposure to the contrast agent may cause kidney diseases or allergic reactions. In addition, being exposed to X-rays may carry a risk of radiation-induced injury and/or of causing cancer.

Further, to reduce the risks incurred due to injection of contrast agent and/or X-ray radiation, the contrast agent dose and/or the radiation dose is kept to a minimum to reduce the risks outlined above. On the other hand, the image quality is reduced as the contrast agent dose and/or the radiation dose reduces. Accordingly, during an angiography exam, the contrast agent dose and/or the radiation dose needs to be controlled in such a way that the image quality is adequate to make a diagnosis whilst keeping the radiation dose as low as reasonably achievable. It is difficult to control the contrast agent dose and/or of the radiation dose during an angiography exam.

SUMMARY

Therefore, a need exists for advanced techniques for angiography exams. Specifically, a need exists for reducing the contrast agent dose and/or the radiation dose. A need exists for angiography providing high quality images.

This need is met by the features of the independent claims. The features of the dependent claims define embodiments.

A computer-implemented method for processing an angiogram is provided. The method includes obtaining one or more frames of an angiogram, which is acquired during an angiography exam of an anatomical region of interest. The method further includes, based on at least one pre-defined criterion, determining, among the one or more frames, whether the angiogram at least includes one frame with a diagnostic value. The method also includes if the angiogram includes at least one frame with the diagnostic value, determining, based on the angiogram, a score using a trained machine-learning, ML, algorithm, wherein the score quantifies the diagnostic value of the angiogram.

A computer-implemented method for processing multiple angiograms is provided. The method includes obtaining multiple angiograms associated with an anatomical region of interest of a patient. The method further includes determining, for each of the multiple angiograms, a score using the method for processing an angiogram mentioned above. The method also includes sorting the multiple angiograms by score descending.

A computing device including a processor and a memory is provided. Upon loading and executing program code from the memory, the processor is configured to perform a method for processing an angiogram. The method includes obtaining one or more frames of the angiogram, which is acquired during an angiography exam of an anatomical region of interest. The method further includes, based on at least one pre-defined criterion, determining, among the one or more frames, whether the angiogram at least includes one frame with a diagnostic value. The method also includes if the angiogram includes at least one frame with the diagnostic value, determining, based on the angiogram, a score using a trained machine-learning, ML, algorithm, wherein the score quantifies the diagnostic value of the angiogram.

A computing device including a processor and a memory is provided. Upon loading and executing program code from the memory, the processor is configured to perform a method for processing multiple angiograms. The method includes obtaining multiple angiograms associated with an anatomical region of interest of a patient. The method further includes determining, for each of the multiple angiograms, a score using the method for processing an angiogram mentioned above. The method also includes sorting the multiple angiograms by score descending.

An angiography device (system) including a computing device (computer) is provided. The computing device includes a processor and a memory. Upon loading and executing program code from the memory, the processor is configured to perform a method for processing an angiogram. The method includes obtaining one or more frames of the angiogram, which is acquired during an angiography exam of an anatomical region of interest. The method further includes based on at least one pre-defined criterion, determining, among the one or more frames, whether the angiogram at least includes one frame with a diagnostic value. The method also includes if the angiogram includes at least one frame with the diagnostic value, determining, based on the angiogram, a score using a trained machine-learning, ML, algorithm, wherein the score quantifies the diagnostic value of the angiogram.

An angiography device including a computing device is provided. The computing device includes a processor and a memory. Upon loading and executing program code from the memory, the processor is configured to perform a method for processing multiple angiograms. The method includes obtaining multiple angiograms associated with an anatomical region of interest of a patient. The method further includes determining, for each of the multiple angiograms, a score using the method for processing an angiogram mentioned above. The method also includes sorting the multiple angiograms by score descending.

A computer program product, a computer program, or a non-transitory computer-readable storage medium including program code is provided. The program code can be executed by at least one processor. Executing the program code causes the at least one processor to perform a method for processing an angiogram. The method includes obtaining one or more frames of the angiogram, which is acquired during an angiography exam of an anatomical region of interest. The method further includes based on at least one pre-defined criterion, determining, among the one or more frames, whether the angiogram at least includes one frame with a diagnostic value. The method also includes if the angiogram includes at least one frame with the diagnostic value, determining, based on the angiogram, a score using a trained machine-learning, ML, algorithm, wherein the score quantifies the diagnostic value of the angiogram.

A computer program product, a computer program or a non-transitory computer-readable storage medium including program code is provided. The program code can be executed by at least one processor. Executing the program code causes the at least one processor to perform a method for processing multiple angiograms. The method includes obtaining multiple angiograms associated with an anatomical region of interest of a patient. The method further includes determining, for each of the multiple angiograms, a score using the method for processing an angiogram mentioned above. The method also includes sorting the multiple angiograms by score descending.

It is to be understood that the features mentioned above and those yet to be explained below may be used not only in the respective combinations indicated, but also in other combinations or in isolation without departing from the scope of the invention.

DETAILED DESCRIPTION OF THE DRAWINGS

Figure 1:
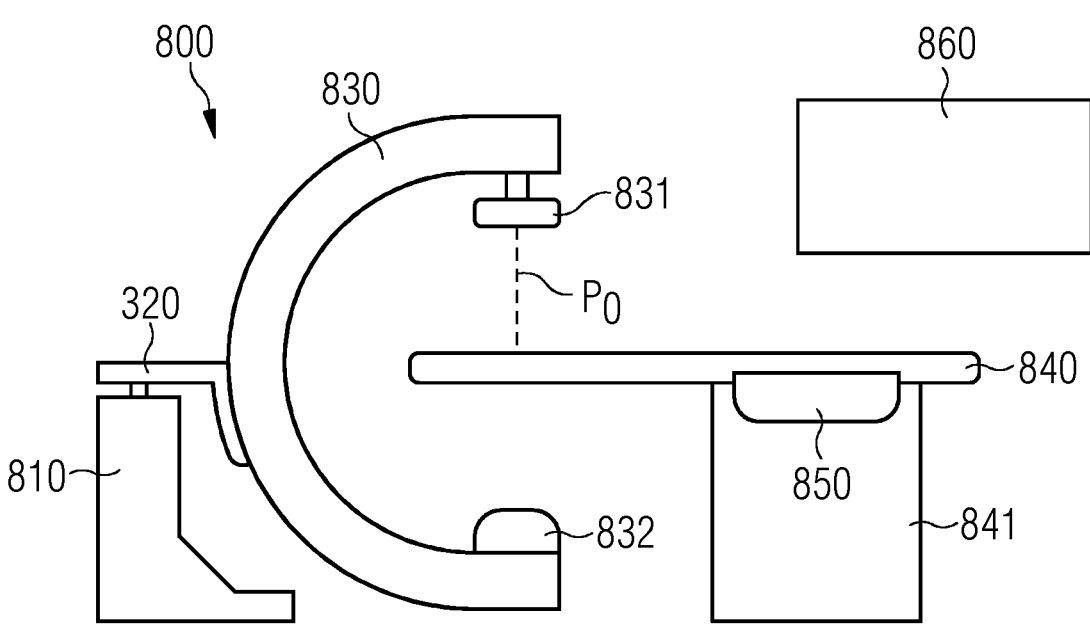
FIG. 1 schematically illustrates aspects with respect to a C-arm machine according to one embodiment.

Some examples of the present disclosure generally provide for a plurality of circuits or other electrical devices. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

In the following, embodiments will be described in detail with reference to the accompanying drawings. It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Hereinafter, techniques of angiography are described. Angiography may be employed to obtain angiograms of an anatomical region of interest, e.g., a region of the heart, the brain, the kidney, or the lung.

According to this disclosure, techniques for processing one or more frames of an angiogram are disclosed. The processing may take place either during or after an angiography exam of an anatomical region of interest, i.e., either real-time processing or post-processing is possible.

The one or more frames of the angiogram are acquired during the angiography exam. The one or more frames are processed to determine, based on at least one pre-defined criterion, whether the angiogram at least includes one frame with a diagnostic value among the one or more frames. If the angiogram includes at least one frame with the diagnostic value, based on the angiogram, a score quantifying the diagnostic value of the angiogram is determined using a trained machine-learning (ML) algorithm.

The diagnostic value can generally describe whether certain features are visible or accurately displayed in the respective frame. The diagnostic value can generally pertain to whether the frame is correctly aligned with a distribution phase of the contrast agent. The diagnostic value can generally correspond to whether a certain frame includes significant artefacts or disturbances.

During the acquisition of an angiogram of an angiography exam, if it is determined that the angiogram does not include any frame with a diagnostic value, one or more appropriate countermeasures may be taken. For example, the acquisition of the (current) angiogram may be stopped and one or more imaging parameters associated with the angiography exam may be adjusted to acquire one or more frames of a further angiogram. The further angiogram may be processed using the same technique as that for processing the (current) angiogram.

Using such techniques, the contrast agent dose and/or the radiation dose can be reduced by stopping the acquisition of the respective angiogram which does not include any frame with a diagnostic value. Further, the (current) angiogram which may not include any frame with a diagnostic value may be discarded, and thereby such an angiogram may not be processed using any one of post-processing algorithms, e.g., vessel layer enhancement algorithms, vessel segmentation algorithms, or stenosis detection algorithms. As such, computational costs incurred by post-processing the angiogram can be reduced.

In addition, the angiogram that includes at least one frame with a diagnostic value is further processed using a trained ML algorithm to determine a score quantifying the diagnostic value of the angiogram. The score can again be used to determine whether one or more countermeasures are to be taken or whether further acquisition is possible. For instance, if the score is below a pre-defined score threshold, the acquisition of the (current) angiogram may be stopped and one or more imaging parameters associated with the angiography exam may be adjusted to acquire one or more frames of a further angiogram. The further angiogram may be processed using the same technique as that for processing the (current) angiogram. Thus, the contrast agent dose and/or the radiation dose can be reduced by stopping the acquisition of the respective angiogram which may not be qualified according to the comparison between the determined score and the pre-defined score threshold. Further, the respective angiogram which may not be qualified may be discarded, and thereby such an angiogram may not be processed using any one of post-processing algorithms. As such, computational costs incurred by post-processing the angiogram can be reduced. On the other hand, if the score equals to or is above the pre-defined score threshold, the angiography exam may be stopped. I.e., no further angiograms may be needed to be acquired once at least one angiogram is determined to achieve a qualified score. As such, the number of angiograms acquired in the angiography exam can be precisely tailored, and thereby the contrast agent dose and/or the radiation dose can be reduced, and the computational costs incurred by post-processing can also be reduced.

In summary, the techniques disclosed herein may utilize a "two-step" processing approach for qualifying and quantifying a diagnostic value of an angiogram to facilitate a reduction of at least one of a contrast agent dose, a radiation dose, and a computational cost incurred by post-processing.

According to various examples, the one or more frames of the angiogram may be obtained directly from an X-ray scanner, e.g., a C-arm machine, or from a database for storing the one or more frames of the angiogram acquired by the X-ray scanner, e.g., a picture archiving and communication system (PACS).

FIG. 1 schematically illustrates aspects with respect to a C-arm machine 800. The C-arm machine 800 may be used for both angiography and fluoroscopy. In FIG. 1, the C-arm machine 800 is in neutral position $P_0$. It is possible to manipulate the C-arm machine 800 to be in a rotated position deviating from the neutral position Po. The angle between the neutral position PO and a specific rotated position is referred to as the angiography angle or the fluoroscopy angle. The C-arm machine 800 includes a rotatable C arm 830 on which X-ray emitter 831 (source) and X-ray detector 832 may be mounted. The C arm 830 and thereby X-ray emitter 831 and X-ray detector 832 are positioned to center around patient surface 840. X-ray emitter 831 may emit X-rays which may penetrate through a patient positioned on patient surface 840. X-ray detector 832 detects the X-rays emitted from X-ray emitter 831. When a patient-on-patient surface 840 is injected with a radio-opaque contrast agent into the patient's vessels, some of the X-rays emitted by X-ray emitter 831 are absorbed by the radio-opaque contrast agent, leading X-ray detector 832 to detect a sequence of images of the vessels filled with the radio-opaque contrast agent, i.e. an angiogram. X-ray emitter 831 and X-ray detector 832 may also collectively be referred to as x-ray imaging means.

The C arm 830 may be coupled to a C arm rotation unit (motor) 820. The C arm rotation unit 820 may be any motorized means configured to rotate the C arm 830 according to an angiography angel or a fluoroscopy angle. The C arm rotation unit 820 may be attached to and controlled by a C arm control until (controller) 810. The C arm control unit 810 may be any kind of circuitry capable of controlling C arm 830. For example, the C arm control unit 810 may include a computing device.

The C-arm machine 800 may further include a control panel 850 mounted onto a side surface of patient surface support 841. The control panel 850 may be used to control C arm 830 in order to guide medical specialists to pathological vessels. FIG. 1 does not show any connections between control panel 850 and C arm 830 to simplify the depiction of the exemplary C-arm machine 800. In some examples, the connection may be wireless. In some further examples, the connection may be wired and may e.g., be integrated into the ceiling of the room where the C-arm machine 800 is located.

The C-arm machine 800 may also include a display 860. The display 860 may be used to display information to the medical specialist, such as real-time fluoroscopy image with an overlaid vessel roadmap image including a path to one or more pathological vessels. Further, the display 860 may be used to display vessel segmentation data included in overlaid vessel roadmap images, including labels for various vessel segments. In some examples, display 860 may be a touch screen, which may be used to toggle the display of the vessel segmentation data on and off.

The C-arm machine 800 may be connectable to a database (not shown in FIG. 1), such as a PACS located within a local network of a hospital, for storing angiograms.

According to this disclosure, various pre-defined criteria may be used to determine, among one or more frames of an angiogram, whether the angiogram at least includes one frame with a diagnostic value. For example, the pre-defined criteria may include at least one of the following:

Criterion 1: whether at least one stenosis in a segment of a blood vessel within the anatomical region of interest can be determined based on a respective frame of the angiogram;

Criterion 2: whether a specific segment of a blood vessel within the anatomical region of interest can be determined based on a respective frame of the angiogram;

Criterion 3: whether the specific segment of the blood vessel includes a contrast above a contrast threshold in at least one frame of the one or more frames of the angiogram;

Criterion 4: whether at least one segment of a blood vessel can be determined based on a respective frame of the angiogram;

Criterion 5: whether blood vessels are blocked by wires or other artefacts.

In general, stenosis refers to any condition in which a blood vessel—such as an artery—or other tubular organ becomes abnormally narrow. The severity of the stenosis for a vessel segment can be assessed visually by a medical imaging expert. More objectively, the percentage of area stenosis can be used to quantify the severity of the stenosis.

According to various examples, a name (e.g., any one in the column "Abbreviation" in Table 1) of a specific segment of a blood vessel within the anatomical region of interest can be determined based on a diagnostic purpose of the angiography exam. For example, such a diagnostic purpose may include that the left or right branch of the coronary vessel tree shall be analyzed, or that a specific vessel section shall be analyzed. The diagnostic purpose may be determined based on user input, or on a patient's electronic medical record included in a health information system.

Figure 2:
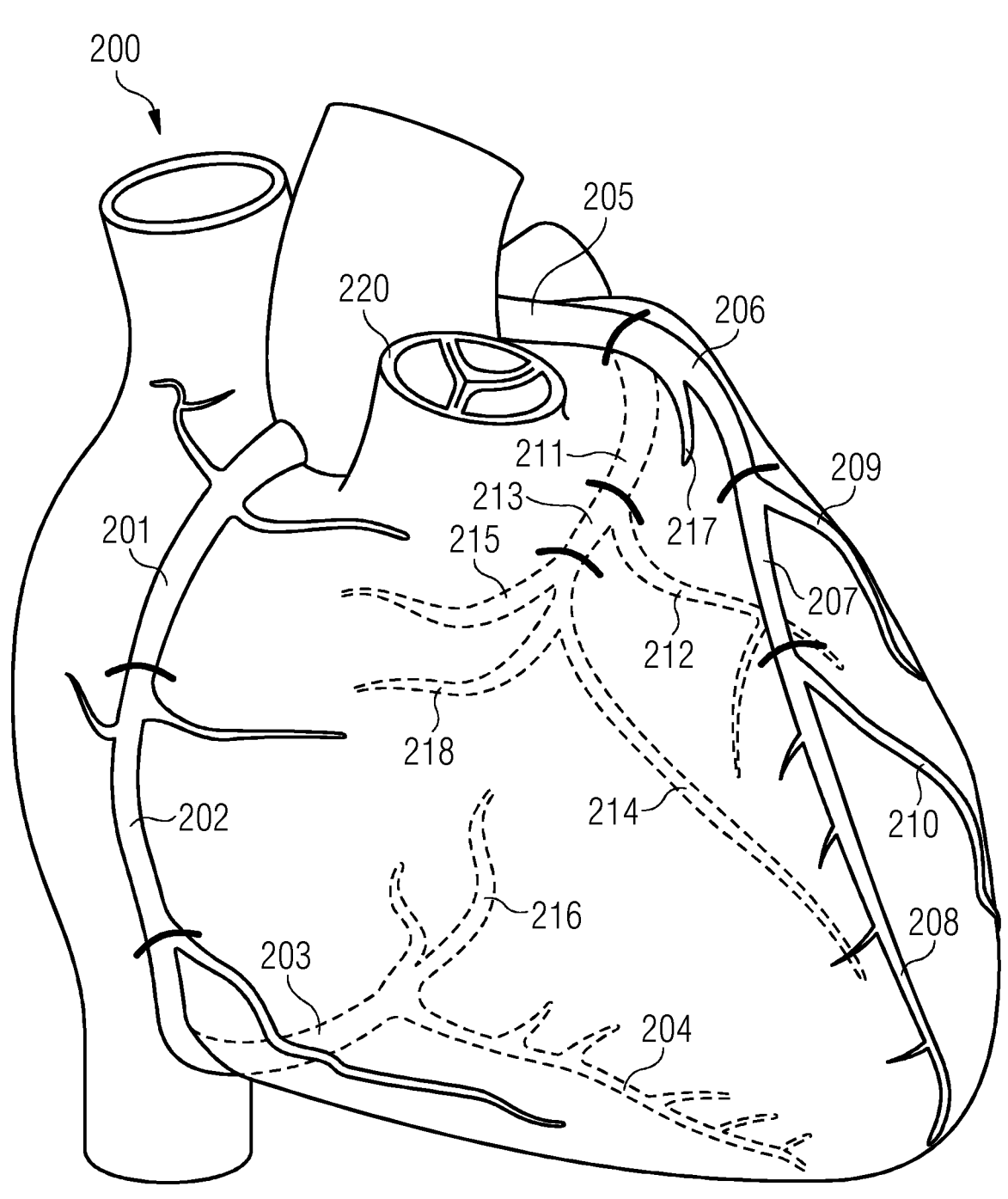
FIG. 2 schematically illustrates an exemplary 3D frontal view of a heart and of coronary arteries.

For example, the specific segment of a blood vessel within the anatomical region of interest may be one segment of the coronary arteries of the heart. FIG. 2 schematically illustrates an exemplary 3D frontal view 200 of a heart and of coronary arteries. The segments of the coronary arteries in FIG. 2 are based on and numbered according to the vessel segmentation as proposed by the American Heart Association (AHA) and as amended by the Society of Cardiovascular Computed Tomography (SCCT). Table 1 provides a short description of the respective vessel segments as well as an abbreviation for each vessel segment.

TABLE 1

Segments of the Coronary Arteries in FIG. 1.

| Ref. Sign | Vessel Segment | Abbreviation | Description |
|---|---|---|---|
| 201 | proximal right coronary artery | pRCA | Ostium of the RCA to one-half the distance to the acute margin of heart |
| 202 | Mid RCA | mRCA | End of pRCA to the acute margin of heart |
| 203 | Distal RCA | dRCA | End of mRCA to origin of the PDA (posterior descending artery) |
| 204 | PDA-R | R-PDA | PDA from RCA |
| 205 | Left main | LM | Ostium of LM to bifurcation of LAD (left anterior descending artery) and LCx (left circumflex artery) |
| 206 | Proximal LAD | pLAD | End of LM to the first large septal or D1 (first diagonal), whichever is most proximal |
| 207 | Mid LAD | mLAD | End of proximal LAD to one-half the distance to the apex |
| 208 | Distal LAD | dLAD | End of mid LAD to end of LAD |
| 209 | D1 | D1 | First diagonal branch D1 |
| 210 | D2 | D2 | Second diagonal branch D2 |
| 211 | Proximal LCx | pCx | End of LM to the origin of the OM1 (first obtuse marginal) |
| 212 | OM1 | OM1 | First OM1 traversing the lateral wall of the left ventricle |
| 213 | Mid and distal LCx | LCx | Traveling in the atrioventricular groove, distal to the OM1 branch to the end of the vessel or origin of the L-PDA |
| 214 | OM2 | OM2 | Second marginal OM2 |
| 215 | PDA-L | L-PDA | PDA from LCx |
| 216 | PLB-R | R-PLB | PLB from RCA |
| 217 | Ramus intermedius | RI | Vessel originating from the left main between the LAD and LCx in case of a trifurcation |
| 218 | PLB-L | L-PLB | PLB from LCx |

In addition to the vessel segments listed in Table 1, FIG. 2 also indicates the aortic valve 220.

According to various examples, any method for solving the ranking problem can be used to determine a score quantifying the diagnostic value of the angiogram. For example, pointwise approach, pairwise approach, listwise approach, or any other approaches disclosed in the non-patent literature—Li, Hang. "A shut introduction to learning to rank." *IEICE TRANSACTIONS on Information and Systems* 94.10 (2011) 1854-1862.

Figure 3:
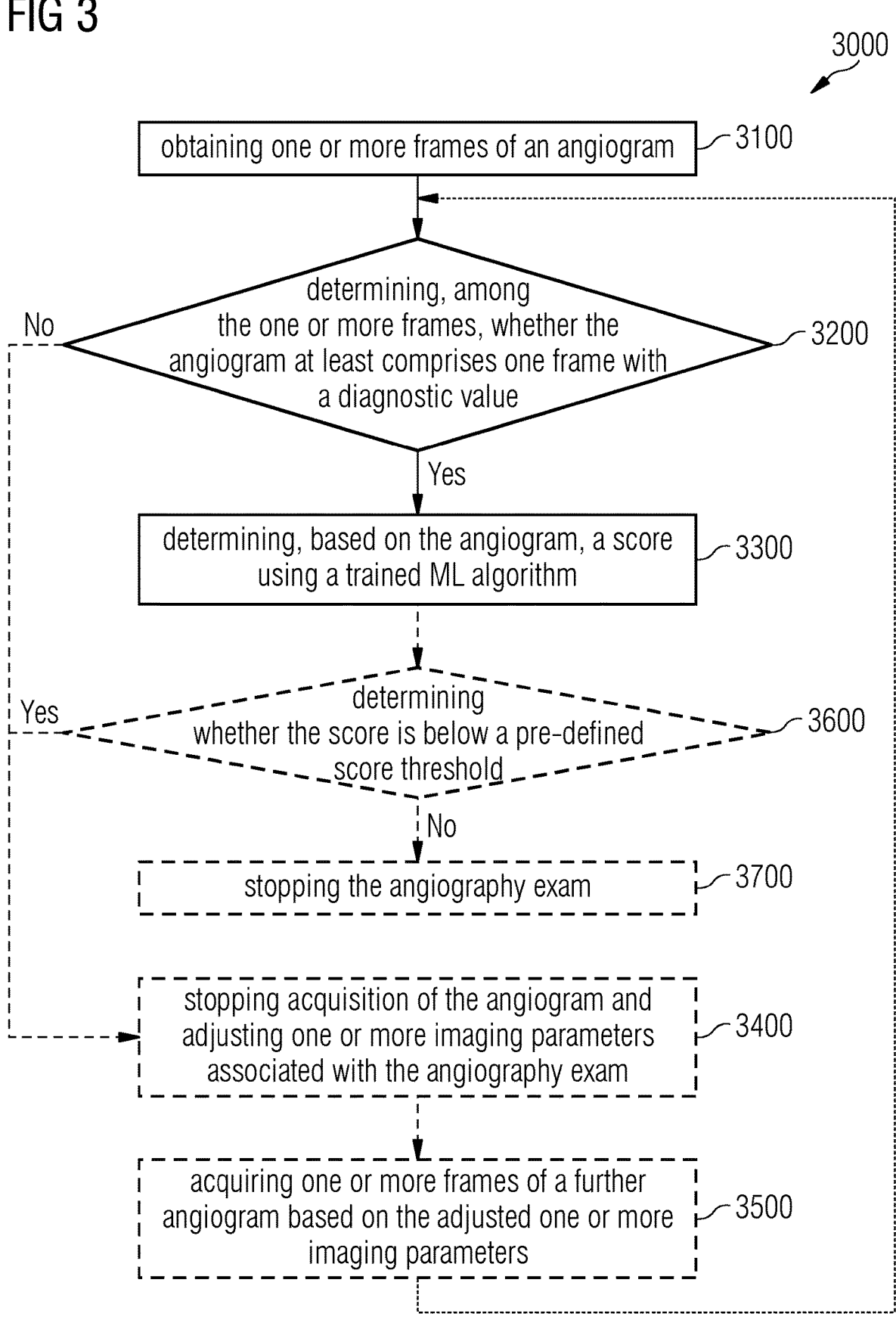
FIG. 3 is a flowchart of a method according to various examples.

FIG. 3 is a flowchart of a method 3000 according to various examples. For example, the method 3000 according to FIG. 3 may be executed by the C arm control unit 810 of the C-arm machine 800 according to the example of FIG. 1, e.g., upon loading program code from a memory. The method 3000 may be executed by the C arm control unit 810 together with the control panel 850, for example, the C arm control unit 810 and the control panel 850 may be together configured to acquire angiograms during an angiography exam of an anatomical region of interest, and the C arm control unit 810 may be further configured to process one or more frames of the acquired angiograms. Further, the method 3000 may be executed by the C arm control unit 810 itself. It would also be possible that the method 3000 is at least partially executed by a separate compute unit, e.g., at a server backend.

FIG. 3 illustrates aspects with respect to processing one or more frames of an angiogram either during or after an angiography exam of an anatomical region of interest (e.g., the heart as shown in FIG. 2), i.e., either real-time processing or post-processing. The one or more frames of the angiogram are acquired during the angiography exam. The one or more frames are processed to determine, based on at least one pre-defined criterion, whether the angiogram at least includes one frame with a diagnostic value among the one or more frames. If the angiogram includes at least one frame with the diagnostic value, based on the angiogram, a score quantifying the diagnostic value of the angiogram is determined using a trained machine-learning (ML) algorithm. Details of the method 3000 are described below.

Optional steps/features are indicated by dashed lines or dashed blocks.

Block 3100: obtaining one or more frames of an angiogram, which is acquired during an angiography exam of an anatomical region of interest.

For example, the one or more frames of the angiogram may be obtained directly from an X-ray scanner, e.g., the C-arm machine 800 of FIG. 1, or from a database for storing the one or more frames of the angiogram acquired by the X-ray scanner, e.g., a PACS. It is possible to select several frames of the angiogram, e.g., 5 or 10 continuous frames starting from the first frame. Frames obtained/acquired in the beginning may be usually of bad quality because the contrast agent may not arrive at a target segment of a blood vessel. Thus, it may be better to select several frames starting from the fifth or eighth frame.

Block 3200: based on at least one pre-defined criterion, determining, among the one or more frames, whether the angiogram at least includes one frame with a diagnostic value.

According to this disclosure, the at least one criterion may include a single criterion, e.g., any one of criteria 1-5. Alternatively, the at least one criterion may include multiple criteria, e.g., any two, three, four of criteria 1-5, or all criteria 1-5. The angiogram may be determined to include at least one frame with the diagnostic value, if all of the multiple criteria can be fulfilled. The more criteria the angiogram can fulfill the higher the score may be determined at block 3300.

According to various examples, the requirements of each of the at least one pre-defined criterion may be assessed using a respective trained (machine learning) ML algorithm (model), e.g., a deep neural network. I.e., each of the at least one pre-defined criterion may be assessed using a respective trained ML algorithm (model). For example, a stenosis detection/classification ML algorithm (model) may be used to assess Criterion 1, and a blood vessel detection/classification ML algorithm (model) may be used to assess Criterion 2.

Block 3300: if the angiogram includes at least one frame with the diagnostic value, determining, based on the angiogram, a score using a trained ML algorithm, wherein the score quantifies the diagnostic value of the angiogram.

It may be determined that the angiogram includes at least one frame with the diagnostic value if each of the at least one criterion is fulfilled. Then, the angiogram is further processed using a trained ML algorithm to determine a score quantifying the diagnostic value of the angiogram. Any approaches for solving the ranking problem available before the filing date of this disclosure can be used to determine the score.

Optionally, the method 3000 may further include, at block 3600, determining whether the score is below a pre-defined score threshold.

If it is determined, at block 3200, that the angiogram includes no frame with the diagnostic value, or at block 3600, that the score is below a pre-defined score threshold, the method 3000 may optionally further include the following two blocks.

Block 3400: stopping acquisition of the angiogram and adjusting one or more imaging parameters associated with the angiography exam.

For example, the one or more imaging parameters may include parameters associated with the C arm 830 (including the left/right anterior oblique (LAO/RAO) angles, the caudal/cranial (CAUD/CRAN) angles, a source-to-image distance (SID), a source-to-object distance (SOD)), parameters associated with the X-ray emitter 831 such as an X-ray tube (including tube potential (kV), tube intensity (mA), exposure time (s) as well as focus to detector distance (cm)), parameters associated with administration of contrast agent (including contrast concentration or volume, and a delivery rate).

Block 3500: acquiring one or more frames of a further angiogram based on the adjusted one or more imaging parameters.

For example, the one or more frames of the further angiogram may be acquired using a new set of imaging parameters and thereby the quality of the one or more frames may be improved.

Optionally or additionally, if it is determined, at block 3200, that the angiogram includes no frame with the diagnostic value, or at block 3600, that the score is below a pre-defined score threshold, the method 3000 may include discarding the angiogram.

By discarding the angiograms which cannot fulfill the at least one criterion, various post-processing workflows or algorithms may not be applied to the discarded angiograms, and thereby computational costs incurred by post-processing the angiogram can be reduced.

Such post-processing workflows or algorithms may include AI (Artificial Intelligence) algorithms to provide analysis for image guidance and/or reporting, algorithms for vessel highlighting, labeling, stenosis localization, and lumen segmentation. It may be important to quickly filter out angiograms either with low diagnostic values or without diagnostic values, which may be generally not selected by clinicians during manual analysis, such as angiograms with low quality, overlap/foreshortening, before sending the respective angiogram to those algorithms. The method 3000 can automatically determine angiograms with a diagnostic value and then determine a score for the angiograms with a diagnostic value.

According to various examples, the one or more frames of the further angiogram obtained at block 3500 may be further processed based on the method 3000, e.g., starting from block 3200. I.e., the method 3000 may be iteratively applied to frames of different angiograms until at least one angiogram is obtained which includes at least one frame with the diagnostic value and achieves a score equaling to or above the pre-defined score threshold.

As such, the method 3000 may optionally further include, at block 3700, stopping the angiography exam, if the score equals to or is above the pre-defined score threshold.

According to various examples, the at least one pre-defined criterion may include whether at least one stenosis in a segment of a blood vessel within the anatomical region of interest can be determined based on a respective frame of the angiogram, i.e., Criterion 1. If the at least one stenosis can be determined based on at least one frame of the one or more frames of the angiogram, the angiogram may be determined to include at least one frame with the diagnostic value.

For example, a further trained ML algorithm may be used to determine whether the at least one stenosis can be determined. The further trained ML algorithm may be a deep neural network, e.g., a multi-label classification network for detecting/determining if any (salient) stenosis is visible in a certain branch/segment of the coronary arteries, e.g., 201-218 of FIG. 2. The further trained ML algorithm may include neural networks disclosed in a non-patent literature—Zhou, Bolei, et al. "Learning deep features for discriminative localization." *Proceedings of the IEEE conference on computer vison and pattern recognition.* 2016.

According to various examples, the at least one pre-defined criterion may include whether a specific segment of a blood vessel (e.g., any one of 201-218 of FIG. 2) within the anatomical region of interest can be determined based on a respective frame of the angiogram, i.e., Criterion 2. If the specific segment of the blood vessel within the anatomical region of interest can be determined based on at least one frame of the one or more frames of the angiogram, the angiogram is determined to include at least one frame with the diagnostic value.

According to various examples, the at least one pre-defined criterion may further include whether the specific segment of the blood vessel includes a contrast above a contrast threshold in at least one frame of the one or more frames of the angiogram, i.e., Criterion 3. If the angiogram includes at least one frame of the one or more frames in which the contrast of the specific segment of the blood vessel is above the contrast threshold, the angiogram may be determined to include at least one frame with the diagnostic value.

According to this disclosure, the score may include a probability that at least one abnormality, e.g., a stenosis, can be diagnosed based on the angiogram.

Optionally or additionally, said determining of the score may be further based on at least one query associated with a diagnosis purpose. For example, the at least one query may include labels of a specific segment of the blood vessel, e.g., any one or more of segments 201-218 of FIG. 2. The at least one query may include a specific branch of the blood vessel, e.g., LAD (i.e., a combination of pLAD 206, mLAD 207, and dLAD 208), or RCA (i.e., a combination of pRCA 201, mRCA 202, and dRCA 203).

Optionally or additionally, the method 3000 may further include training both the ML algorithm and the further ML algorithm. According to the disclosure, various training methods of ML algorithm may be applied to train either the ML algorithm or the further ML algorithm, such as supervised learning, unsupervised learning, semi-supervised learning, self-supervised learning, reinforcement learning and etc.

For example, to generate a dataset for training, a large dataset can be filtered to generate candidates and the candidates can be manually ranked/scored by experts based on a respective diagnostic value. Therefore, experts' experience/preferences can be directly included in the ranking/scoring method 3000. In addition to the expert's experience/preference, additional ranking signals for training can be derived from the algorithms that perform further post-processing. For example, some algorithms may generate measures of confidence for their primary outputs (e.g., stenosis detection) as secondary outputs, which may be correlating with the "quality" of angiograms from the algorithm's perspective (i.e., how well can the algorithm process this specific angiogram; which may depend on how algorithms themselves were trained/developed). Such confidence measures can be used to favor sequences/angiograms in the ranking/scoring training that the algorithms are able to process with good accuracy.

The method 3000 may utilize a "two-step" processing approach for qualifying and quantifying a diagnostic value of an angiogram to facilitate a reduction of at least one of a contrast agent dose, a radiation dose, and a computational cost incurred by post-processing the angiogram.

According to this disclosure, it is possible to utilize the method 3000 for processing one or more frames of an angiogram during the acquisition of the angiogram or after the acquisition of the angiogram. Details with respect to several use cases of the method 3000 will be described below.

Inline Application of the Method 3000:

The method 3000 can be executed during the acquisition of an angiogram to optimize at least one of exam time, delivery of radiation dose, and administration of contrast agent.

Example 1

Example 1 may include starting acquisition of an angiogram; selecting a subsequence of the acquired frames of the angiogram; applying the method 3000 to the subsequence. If the subsequence meets the pre-defined criteria, stop delivery of radiation or switch from angiography settings to fluoroscopy settings.

Example 2

Example 2 may include starting acquisition of an angiogram; selecting a subsequence of the acquired frames of the angiogram; applying the method 3000 to the subsequence. If the subsequence achieves a score below a pre-defined score threshold, stop delivery of radiation or switch from angiography settings to fluoroscopy settings.

Further, the method 3000 can be used to advise the operator on the need to acquire additional angiograms, e.g., a further angiogram.

Example 3

Example 3 may include acquiring one angiogram; applying the method 3000 to the angiogram either inline or after the acquisition is completed. If the angiogram achieves a score below a pre-defined score threshold, advise the operator to acquire a further angiogram.

The method 3000 can perform more advanced filtering of angiograms based on at least one pre-defined criterion and select angiograms with a high diagnostic value for further processing, e.g., real-time processing or post-processing. Therefore, the amount of time for the overall workflow of acquiring and processing angiograms can be reduced.

Figure 4:
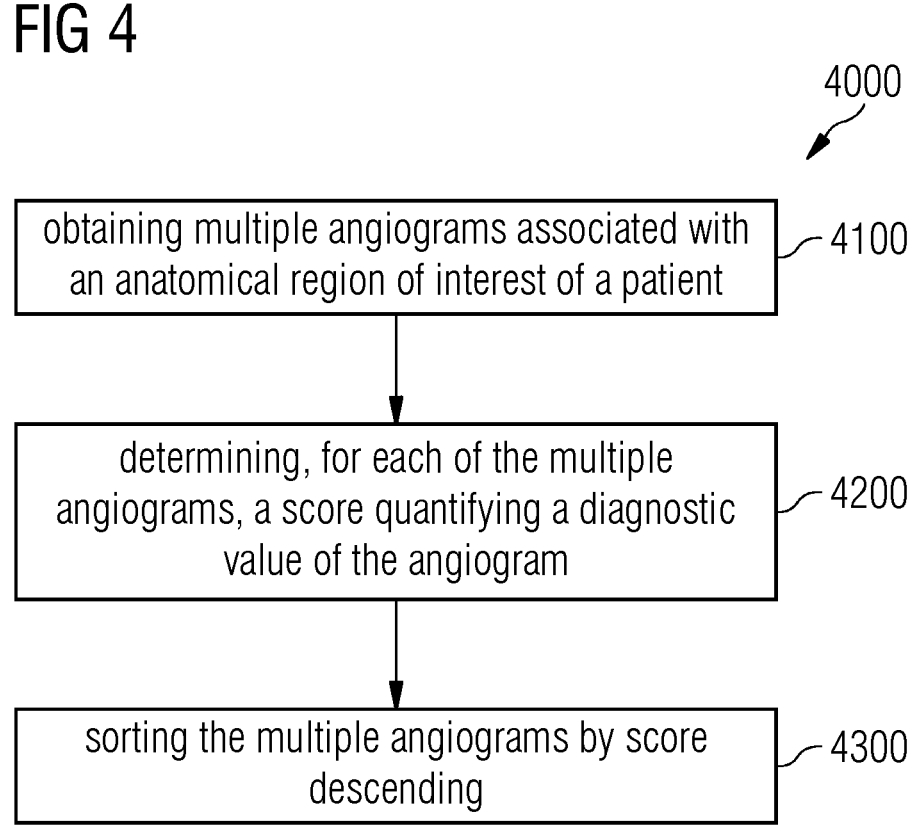
FIG. 4 is a flowchart of a further method according to various examples.

FIG. 4 is a flowchart of a further method 4000 according to various examples. For example, the method 4000 according to FIG. 4 may be executed by the C arm control unit 810 of the C-arm machine 800 according to the example of FIG. 1, e.g., upon loading program code from a memory. The method 4000 may be executed by the C arm control unit 810 together with the control panel 850, for example, the C arm control unit 810 and the control panel 850 may be together configured to acquire angiograms during an angiography exam of an anatomical region of interest, and the C arm control unit 810 may be further configured to process one or more frames of the acquired angiograms. Further, the method 4000 may be executed by the C arm control unit 810 itself. It would also be possible that the method 4000 is at least partially executed by a separate compute unit, e.g., at a server backend.

FIG. 4 illustrates aspects with respect to processing multiple angiograms associated with an anatomical region of interest of a patient. For each of the multiple angiograms, a respective score quantifying the diagnostic value of the respective angiogram is determined using the method 3000 of FIG. 3. Then, the multiple angiograms are sorted by score descending or ascending. Details of the method 4000 are described below.

At block 4100: obtaining multiple angiograms associated with an anatomical region of interest of a patient.

For example, the multiple angiograms may be obtained directly from an X-ray scanner, e.g., the C-arm machine 800 of FIG. 1, or from a database for storing angiograms acquired by the X-ray scanner, e.g., a PACS.

At block 4200: determining, for each of the multiple angiograms, a score using the method 3000 of FIG. 3.

At block 4300: sorting the multiple angiograms by score descending or ascending.

Optionally or additionally, the method 4000 may further include displaying and/or processing the multiple angiograms in an order associated with the sorting.

According to various examples, after scoring and sorting (or ranking) each of the multiple angiograms, the results of the sorting can be used to define an order of the then fully-processed angiograms shown to the user. For example, the angiogram with the highest score may be displayed to a user, or the two or three angiograms with the highest score may be selected for post-processing.

Figure 5:
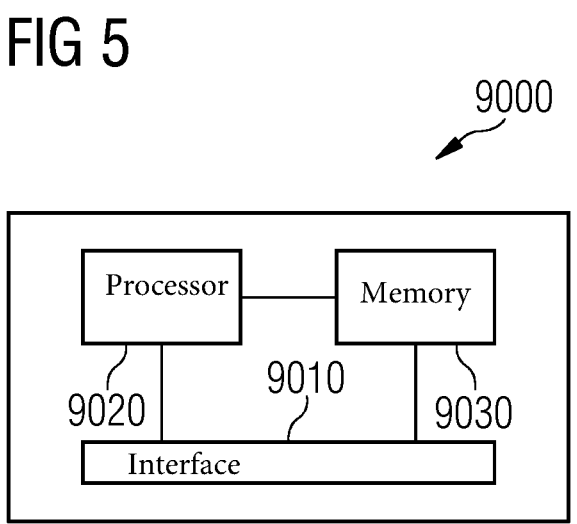
FIG. 5 is a block diagram of a computing device according to various examples.

FIG. 5 is a block diagram of a computing device 9000 according to various examples. The computing device 9000 may include a processor 9020, a memory 9030, and an input/output interface 9010. The processor 9020 is configured to load program code from the memory 9030 and execute the program code. Upon executing the program code, the processor 9020 performs the method 3000 for processing one or more frames of an angiogram and/or the method 4000 for processing multiple angiograms.

The computing device 9000 may be embedded in or connected with an angiography device such as the C-arm machine 800. I.e., the angiography device including the computing device 9000 may be configured to perform the method 3000 and/or the method 4000.

Referring to FIG. 1 again, the C-arm machine 800 may further include the computing device 9000 configured to perform either the method 3000 or the method 4000. The computing device 9000 may be the C arm control unit (controller) 810 and/or the control panel 850. I.e., the computing device 9000 may be embedded in or connected with the C-arm machine 800, and thereby the C-arm machine 800 may be also configured to perform the method 3000 and/or the method 4000.

Summarizing, techniques have been described that facilitate processing angiograms. Specifically, the techniques disclosed herein may utilize a "two-step" processing approach for qualifying and quantifying a diagnostic value of an angiogram to facilitate a reduction of at least one of a contrast agent dose, a radiation dose, and a computational cost incurred by post-processing.

Although the disclosure has been shown and described with respect to certain preferred embodiments, equivalents and modifications will occur to others skilled in the art upon the reading and understanding of the specification. The present disclosure includes all such equivalents and modifications and is limited only by the scope of the appended claims.

For illustration, the disclosure is explained in detail based on coronary angiography. The techniques disclosed herein can be also applied to other angiography techniques, such as cerebral angiography, pulmonary angiography, renal angiography, and fluorescein angiography.

Further, the techniques disclosed herein can be also applied to angiography that may be done using scans instead of X-rays, such as CT (computed tomography) angiography or MRI (Magnetic resonance imaging) angiography.

The invention claimed is:

1. A computer-implemented method comprising:
obtaining one or more frames of an angiogram, which angiogram is acquired during an angiography exam of an anatomical region of interest;
based on at least one pre-defined criterion, determining, among the one or more frames, whether the angiogram at least comprises one frame with a diagnostic value, wherein the at least one pre-defined criterion comprises whether at least one stenosis in a segment of a blood vessel within the anatomical region of interest can be determined based on a respective frame of the angiogram, wherein when the at least one stenosis is determined based on at least one frame of the one or more frames of the angiogram, the angiogram is determined to comprise at least one frame with the diagnostic value; and
when the angiogram comprises at least one frame with the diagnostic value, determining, based on the angiogram, a score using a trained machine-learning algorithm, wherein the score quantifies the diagnostic value of the angiogram.

2. The computer-implemented method of claim 1, further comprising:
when the angiogram comprises no frame with the diagnostic value or if the score is below a pre-defined score threshold, stopping acquisition of the angiogram and adjusting one or more imaging parameters associated with the angiography exam, and acquiring one or more frames of a further angiogram based on the adjusted one or more imaging parameters.

3. The computer-implemented method of claim 2, further comprising:
discarding the angiogram.

4. The computer-implemented method of claim 1, further comprising:
when the score equals to or is above a pre-defined score threshold, stopping the angiography exam.

5. The computer-implemented method of claim 1, wherein a further trained ML algorithm is used to determine whether the at least one stenosis can be determined.

6. The computer-implemented method of claim 1, wherein the at least one pre-defined criterion further comprises whether a specific segment of a blood vessel within the anatomical region of interest can be determined based on a respective frame of the angiogram; and
when the specific segment of the blood vessel within the anatomical region of interest can be determined based on at least one frame of the one or more frames of the angiogram, the angiogram is determined to comprise at least one frame with the diagnostic value.

7. The computer-implemented method of claim 6, wherein the at least one pre-defined criterion further comprises whether the specific segment of the blood vessel comprises a contrast above a contrast threshold in at least one frame of the one or more frames of the angiogram;
when the angiogram comprises at least one frame of the one or more frames in which the contrast of the specific segment of the blood vessel is above the contrast threshold, the angiogram is determined to comprise at least one frame with the diagnostic value.

8. The computer-implemented method of claim 1, wherein the score comprises a probability that at least one abnormality can be diagnosed based on the angiogram.

9. The computer-implemented method of claim 1, wherein determining of the score is further based on at least one query associated with a diagnosis purpose.

10. A computer-implemented method comprising:
obtaining multiple angiograms associated with an anatomical region of interest of a patient;
determining, based on at least one pre-defined criterion comprising whether at least one stenosis in a segment of a blood vessel within the anatomical region of interest can be determined based on a respective frame of the angiogram, whether the respective angiogram of the multiple angiograms comprises at least one frame with a diagnostic value, wherein when the at least one stenosis is determined based on at least one frame of the one or more frames of the angiogram, the respective angiogram is determined to comprise at least one frame with the diagnostic value;
determining, for each of the multiple angiograms that comprise at least one frame with diagnostic value, a score using a trained machine-learning algorithm, wherein the score quantifies the diagnostic value of the respective angiogram; and
sorting the multiple angiograms by score descending.

11. The computer-implemented method of claim 10, further comprising:
displaying and/or processing the multiple angiograms in an order associated with the sorting.

12. The computer-implemented method of claim 10, further comprising:

when one of the scores equals to or is above a pre-defined score threshold, stopping the angiography exam.

13. The computer-implemented method of claim 10, wherein the score comprises a probability that at least one abnormality can be diagnosed based on the angiogram.

14. An angiography system comprising:

a memory configured to store program code; and a processor configured to execute the program code, the processor being configured by the program code to:

obtain one or more frames of an angiogram, which angiogram is acquired during an angiography exam of an anatomical region of interest;

based on at least one pre-defined criterion, determine, among the one or more frames, whether the angiogram at least comprises one frame with a diagnostic value, wherein the at least one pre-defined criterion comprises whether a specific segment of a blood vessel within the anatomical region of interest can be determined based on a respective frame of the angiogram, wherein when the specific segment of the blood vessel within the anatomical region of interest can be determined based on at least one frame of the one or more frames of the angiogram, the angiogram is determined to comprise at least one frame with the diagnostic value; and when the angiogram comprises at least one frame with the diagnostic value, determine, based on the angiogram, a score using a trained machine-learning algorithm, wherein the score quantifies the diagnostic value of the angiogram.

15. The angiography system of claim 14, wherein the processor is configured to, when one of the scores equals to or is above a pre-defined score threshold, stop the angiography exam.

16. The angiography system of claim 14, wherein the score comprises a probability that at least one abnormality can be diagnosed based on the angiogram.

17. The angiography system of claim 14, wherein the processor is configured to, when the angiogram comprises no frame with the diagnostic value or if the score is below a pre-defined score threshold, stop acquisition of the angiogram and adjust one or more imaging parameters associated with the angiography exam, and acquire one or more frames of a further angiogram based on the adjusted one or more imaging parameters.

* * * * *